United States Patent [19]

Hite et al.

[11] Patent Number: 5,283,361
[45] Date of Patent: Feb. 1, 1994

[54] N-HYDROXY-N-[3-[2-(HALOPHENYLTHIO)-PHENYL]PROP-2-ENYL]UREAS AS LIPOXYGENASE INHIBITORS

[75] Inventors: Gary A. Hite, Indianapolis; Edward D. Mihelich, Carmel; David W. Snyder, Indianapolis; Tulio Suarez, Greenwood, all of Ind.

[73] Assignee: Eli Lilly and Company, Indianapolis, Ind.

[21] Appl. No.: 865,005

[22] Filed: Apr. 8, 1992

Related U.S. Application Data

[63] Continuation of Ser. No. 690,204, Apr. 23, 1991, abandoned.

[51] Int. Cl.$^5$ ............... C07C 275/02; C07C 275/24; A61K 31/17; A61K 31/185

[52] U.S. Cl. ................................. 562/623; 564/47; 564/56

[58] Field of Search ............... 562/623; 514/575, 595

[56] References Cited

FOREIGN PATENT DOCUMENTS 0384594 8/1990 European Pat. Off. .

Primary Examiner—José G. Dees
Assistant Examiner—B. Frazier
Attorney, Agent, or Firm—Roger S. Benjamin; Leroy Whitaker; John C. Demeter

[57] ABSTRACT

This invention relates to N-hydroxy-N-[3-[2-(4'-halophenylthio)phenyl]prop-2-enyl]ureas, formulations containing those compounds and methods of using such compounds as 5-lipoxygenase inhibiting agents.

25 Claims, No Drawings

N-HYDROXY-N-[3-[2-(HALOPHENYLTHIO)-PHENYL]PROP-2-ENYL]UREAS AS LIPOXYGENASE INHIBITORS

This application is a continuation of application Ser. No. 07/690,204 filed Apr. 23, 1991, now abandoned.

BACKGROUND OF THE INVENTION

This invention relates to certain N-hydroxy-N-[3-[2-(halophenylthio)phenyl]prop-2-enyl]ureas, compositions containing those compounds and methods of their use.

The enzyme 5-lipoxygenase (5-LO) catalyzes the first step of a biochemical synthesis pathway by which arachidonic acid is converted into leukotrienes. Numerous and extremely potent biological activities have been associated with leukotrienes. Leukotrienes have been implicated as important mediators in a variety of disease states such as asthma, arthritis, psoriasis, ischemia, allergy, adult respiratory distress syndrome (ARDS), and inflammatory bowel disease (IBD).

Considerable efforts have been directed toward the control of leukotriene biosynthesis. Generally research efforts directed toward the control of leukotriene biosynthesis have been directed toward the discovery of inhibitors of the 5-LO pathway and, in particular, 5-LO specific inhibitors.

In U.K. Patent Application GB 2,196,629 certain ring substituted-N-hydroxy-N-substituted benzamide and cinnamamide compounds are disclosed as antileukotriene agents. The ring substituent may be a group having the Formula (Ra) (Rb) C=CH— where (Ra) (Rb)C= is an unsaturated aliphatic hydrocarbylene group containing 3 to 19 carbon atoms, a group having the Formula $R_3$—C≡C— where $R_3$ is a hydrogen atom or a saturated or unsaturated aliphatic hydrocarbyl group containing 1 to 18 carbon atoms or a group having the formula $R_4$—S— where $R_4$ is an aliphatic hydrocarbyl group containing 1 to 20 carbon atoms. The N-substituent may be a $C_1$-$C_6$ alkyl group, a $C_3$-$C_7$ cycloalkyl group or a substituted or unsubstituted aryl group.

In European Patent Application 0196184 certain aryl compounds are disclosed which include, among many others, certain cinnamohydroxamic acid analogs and certain N-hydroxyureas in Examples 81-91. Certain urea based or urea containing compounds that are said to inhibit lipoxygenase are disclosed in EPO 0292699; EPO 0279281; and EPO 0279263. These references contain no recognition of the importance of a 3-[2-(halophenylthio)phenyl]prop-2-enyl substituted on a urea skeleton.

In WO 90/12008 certain unsubstituted and substituted phenyl, naphthyl and thienyl N-hydroxy ureas are disclosed as inhibitors of 5- and 12-lipoxgenase. The preparation and biological activity for a number of such derivatives is disclosed. The present invention is directed to the discovery that a select group of N-hydroxy-N-[3-[2-[4-halophenylthio)phenyl]-prop-2-enyl]ureas are extremely potent 5-LO inhibitors. The compounds of the present invention, as defined herein, are surprisingly advantageous inhibitors of 5-LO and have useful medical prophylactic and therapeutic properties. The compounds of the present invention and their pharmaceutically acceptable salts possess surprisingly high potency.

Accordingly, it is a primary object of the present invention to provide surprisingly potent selective 5-LO inhibitors useful in the treatment of asthma and allergic diseases, inflammatory bowel disease, psoriasis, shock, ischemia, adult respiratory distress syndrome (ARDS) and arthritis.

A further object of the present invention is to provide therapeutic compositions for treating said diseases and disorders.

Still another object is to provide methods for treating said diseases and disorders.

Other objects, features and advantages will become apparent to those skilled in the art from the following description and claims.

SUMMARY OF THE INVENTION

The present invention provides N-hydroxy-N-[3-[2-(halophenylthio)phenyl]prop-2-enyl]ureas of the Formula

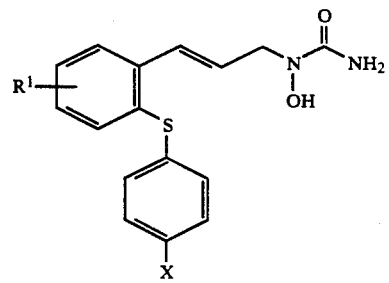

where
$R^1$ is hydrogen or halo;
X is fluoro or chloro; and pharmaceutically acceptable salts thereof.

In addition to the compounds of Formula I, the present invention provides pharmaceutical formulations comprising a compound of Formula I in association with a pharmaceutically acceptable carrier, diluent or excipient.

The present invention also provides a method of treating asthma, allergic diseases, inflammatory bowel disease, psoriasis, shock, ARDS and arthritis in mammals comprising administering to a mammal in need of such treatment a 5-LO inhibiting dose of a compound according to Formula I.

The present invention further provides a process for preparing 2-[2-(4-halophenylthio)phenyl]-4,4-dimethyloxazoline intermediates useful in preparing compounds of Formula I.

DETAILED DESCRIPTION OF THE INVENTION

The following compounds illustrate compounds contemplated within the scope of Formula I:
N-hydroxy-N-[3-[2-(4-fluorophenylthio)-6-fluorophenyl]prop-2-enyl]urea
N-hydroxy-N-[3-[2-(4-chlorophenylthio)phenyl]prop-2-enyl]urea
N-hydroxy-N-[3-[2-(4-fluorophenylthio)-5-fluorophenyl]prop-2-enyl]urea
N-hydroxy-N-[3-[2-(4-fluorophenylthio)-4-fluorophenyl]prop-2-enyl]urea
N-hydroxy-N-[3-[2-(4-fluorophenylthio)-3-fluorophenyl]-prop-2-enyl]urea N-hydroxy-N-[3-[2-(4-fluorophenylthio)phenyl]prop-2-enyl]urea N-hydroxy-N-[3-[2-(4-chlorophenylthio)-3-fluorophenyl]prop-2-enyl]urea N-hydroxy-N-[3-[2-(4-chlorophenylthio)-6-fluorophenyl]prop-2-enyl]urea The compounds of the present invention or their precursors can be prepared according to the following processes.

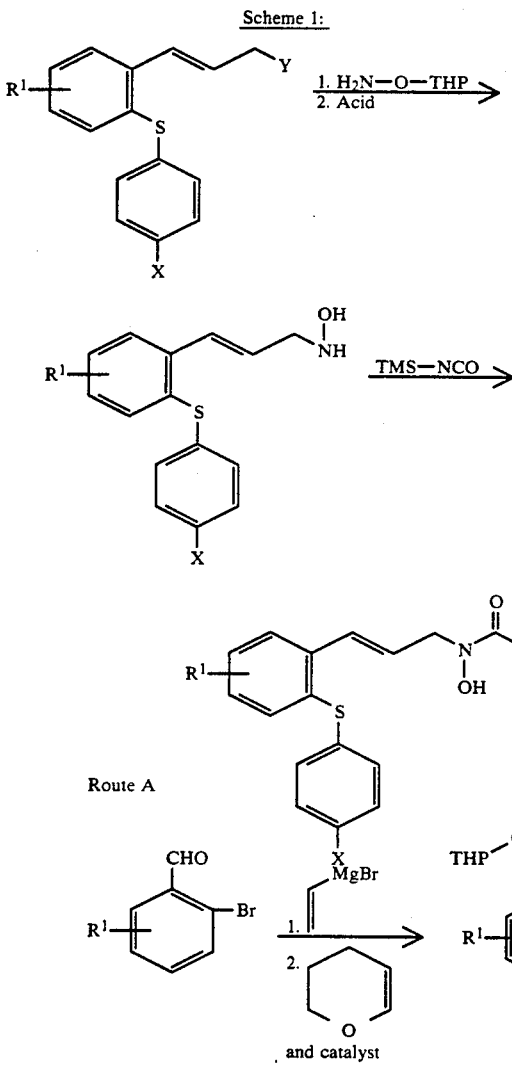

Route A where Y is bromo or chloro; THP is tetrahydropyranyl; TMS is trimethylsilyl; and $R_1$ and X are as defined above for Formula I.

In Scheme 1, a 2-halophenylthio cinnamyl halide is reacted with o-tetrahydropyranyl hydroxylamine which can be isolated or further reacted with an acid in an inert or substantially inert solvent or mixture of solvents to afford the corresponding N-cinnamyl-N-hydroxylamine. The N-(2-halophenylthio cinnamyl)-N-hydroxyamine afforded can be isolated or further reacted with a trimethylsilyl isocyanate in an inert or substantially inert solvent or mixture of solvents to afford the desired compound of Formula I.

Suitable solvents for use in the first reaction of the above process are aprotic solvents, preferably dimethylformamide.

This reaction can be carried out at temperatures between about 0° C. and about 50° C. Preferably, this reaction is carried out at about room temperature.

Suitable acids for use in the second reaction are inorganic acids and preferably concentrated HCl.

Suitable solvents for use in the second reaction include protic solvents and preferably methanol.

The second reaction can be carried out at temperatures between about 0° C. and about 30° C. Preferably, the reaction is carried out at about room temperature.

Suitable solvents for the isocyanate condensation reaction include ethers and preferably dioxane. This reaction can be carried out at temperatures between about 0° C. and about 50° C. preferably room temperature. The H₂NOTHP reactant was prepared according to procedures described in *Angew. Chem.*, Int. Ed., 5, 511 (1966).

The 2-halophenylthio cinnamyl halides in Scheme 1, to the extent they are not commercially available, are obtained by any of several routes shown below in Schemes 2 and 3, using procedures well-known to those skilled in the art.

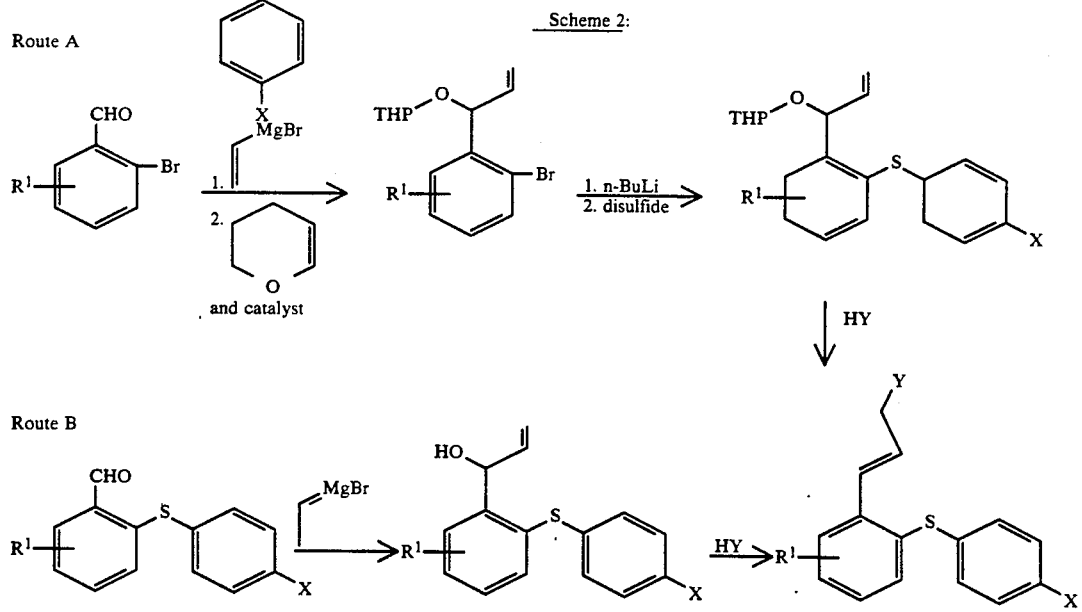

Scheme 2 shows routes beginning with a substituted benzaldehyde. In Route B, a 2-halophenylthio benzaldehyde is reacted with a vinyl Grignard reagent in an inert or substantially inert solvent or mixture of solvents to afford the corresponding 1-hydroxy-1-(2-halophenylthio phenyl)prop-2-ene which may be isolated or further reacted as described below. This reaction is carried out under standard conditions for a Grignard reaction which are known to those skilled in the art. Similarly, in Route A, a 2-bromobenzaldehyde is reacted with a vinyl Grignard reagent in an inert or substantially inert solvent or mixture of solvents to afford the corresponding 1-(2-bromophenyl)prop-2-en-ol which may be isolated or further reacted with a suitable alcohol protecting group, preferably dihydropyran in the presence of a catalyst, preferably $POCl_3$ to afford the corresponding 1-tetrahydropyranyloxy-1-(2-bromophenyl)prop-2-ene. The 1-tetrahydropyranyloxy-1-(2-bromophenyl)prop-2-ene may be isolated or undergo a substitution reaction at the 2-position in an inert or substantially inert solvent or mixture of solvents to afford the corresponding 1-tetrahydropyranyloxy-1-(2-halophenylthiophenyl)prop-2-ene which may be isolated or hydrolyzed with acid in an inert or substantially inert solvent or mixture of solvents to afford a 2-halophenylthio cinnamyl halide.

The vinyl Grignard reagent condensation is carried out under standard conditions for a Grignard reaction which are known to those skilled in the art. Although tetrahydropyranyl is shown in Scheme 2, Route A, any of a number of base-stable alcohol protecting groups may be used such as tetrahydropyranyloxy, methoxyethoxymethyl, methoxymethyl, silyl and others. The reaction is carried out in an inert or substantially inert solvent or mixture of solvents in the presence of an appropriate acid or base catalyst, depending on the alcohol protecting group, which are well known to those skilled in the art. The substitution reaction is carried out by sequentially treating the 1-tetrahydropyranyloxy-1-(2-bromophenyl)prop-2-ene with a ($C_1$-$C_4$) alkyllithium reagent and with the appropriate phenyl disulfide. Suitable solvents for the substitution reaction are aprotic ethers such as diethyl ether and preferably tetrahydrofuran. The reaction is carried out between about $-100°$ C. to about $-40°$ C., preferably between about $-55°$ C. and about $-85°$ C.

In each of Routes A and B in Scheme 2, the intermediate compound is reacted with a concentrated acid, preferably inorganic such as HCl or HBr to afford the 2-halophenylthiocinnamyl halide intermediate.

To the extent not commercially available, the initial compounds for Routes A and B can be prepared by reactions both apparent and well known to those skilled in the art. Alternatively, and preferably, the starting compound for Route B can be obtained as shown below in Scheme 3.

Scheme 3:

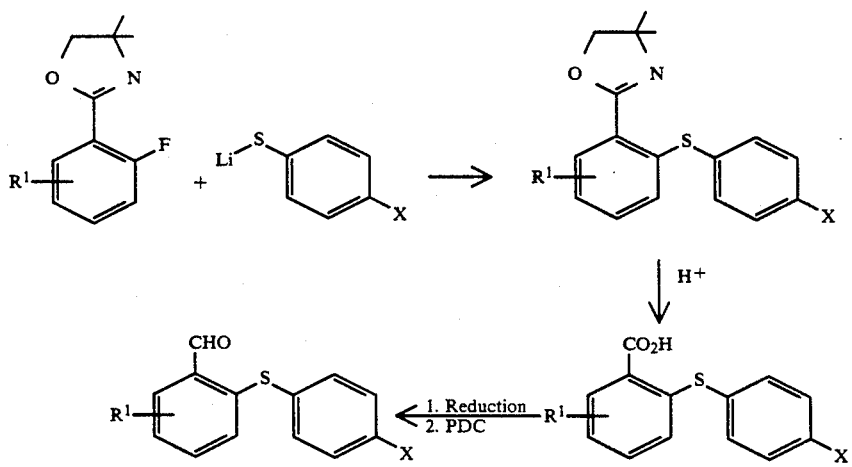

In Scheme 3,4-halothiophenol is treated with a ($C_1$-$C_4$) alkyl lithium reagent such as methyllithium, n-butyllithium, sec-butyllithium and t-butyllithium in an aprotic solvent, including ethers such as tetrahydrofuran and diethyl ether, preferably tetrahydrofuran at a temperature of from about $-40°$ C. to about $-100°$ C., preferably from about $-55°$ C. to about $-85°$ C., to afford the corresponding lithium thiolate. The lithium thiolate is reacted with a 2-(2-fluorophenyl)-4,4-dimethyloxazoline in an aprotic solvent including ethers such as THF and diethyl ether, preferably THF, at a temperature of from about $0°$ C. to about $100°$ C., preferably at from about $20°$ C. to about $70°$ C. to afford an ortho 4-halophenylthio substituent on the phenyl ring.

The 2-oxazoline is then hydrolyzed using 4.5N HCl where the 2-oxazoline is at a concentration of about 0.05M and refluxing to afford the corresponding 2-(4-halophenylthio) benzoic acid which is reduced with lithium aluminum hydride, or other suitable hydride reducing agent in an inert or substantially inert solvent or mixture of solvents to afford the corresponding alcohol which may be isolated or further reacted with pyridinium dichromate in a suitable inert or substantially inert solvent or mixture of solvents to afford a 2-(4-halophenylthio)benzaldehyde.

Alternatively, the 2-oxazoline may be quarternized by reacting it with methyl iodide which is then reduced with sodium borohydride or other suitable hydride reducing agent in a suitable inert or substantially inert solvent or mixture of solvents and then hydrolyzed with 3N HCl to afford a 2-(halophenylthio)benzaldehyde.

The present invention further contemplates a process for preparing a 2-[2-(4-halophenylthio)phenyl]-4,4-dimethyloxazoline having the formula

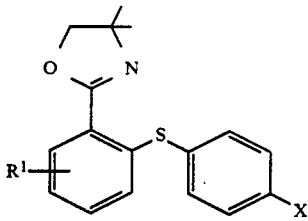

where:
R¹ is hydrogen or halo and X is fluoro or chloro comprising:
a) reacting 4-fluorothiophenol or 4-chlorothiophenol with a C1–C4 alkyllithium reagent in an aprotic solvent at a temperature of from about −40° C. to about −100° C. to afford a corresponding lithium thiolate; and
b) reacting the lithium thiolate from (a) with a 2-(2-fluorophenyl)-4,4-dimethyloxazoline having the formula

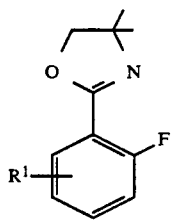

where: R1 is hydrogen or halo in an aprotic solvent at a temperature of from about 0° C. to about 100° C. to afford said 2-[2-(4-halophenylthio)phenyl]-4,4-dimethyloxazoline.

The phrase "inert or substantially inert solvents" are substances that provide a medium in which a reaction can occur but otherwise do not materially contribute to the reaction.

Modifications to the above processes may be necessary to accommodate reactive functionalities of particular substituents. Such modifications would be both apparent and known to those skilled in the art.

As mentioned above, the invention includes pharmaceutically acceptable salts of the compounds defined by Formula I. Although generally neutral, a particular compound of this invention may possess a sufficiently acidic or basic functional group to react with any of a number of nontoxic inorganic bases, and nontoxic inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluene-sulfonic, methanesulfonic acid, oxalic acid, p-bromo-phenyl-sulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from alkali or alkaline earth metal hydroxides, carbonates, bicarbonates, and the like. Such bases useful in preparing the salts of this invention thus include sodium hydroxide, potassium hydroxide, potassium carbonate, sodium carbonate, sodium bicarbonate, potassium bicarbonate, calcium hydroxide, calcium carbonate, and the like. The potassium and sodium salt forms are particularly preferred.

It is recognized that various isomeric forms of the compounds of Formula I may exist. This invention is not limited to any particular isomer but rather includes all possible individual isomers and mixtures thereof.

The compounds of Formula I and the pharmaceutically acceptable salts thereof can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent. These solvates are also within the scope of the present invention.

The pharmaceutically acceptable salts embraced by Formula I of the present invention are prepared by reacting an equimolar or excess amount of an acid or base with a compound of Formula I in a suitable mutual inert or substantially inert solvent or a mixture of solvents. The particular choice of solvent will depend on the relative solubility of the starting materials and resultant salts, and slurries rather than solutions of certain reagents may be used to obtain the salts. The salt forming reaction is carried out at about −10° C. to about 100° C., preferably about room temperature and the solvent is removed by conventional means.

The following examples will further illustrate this invention but are not intended to limit it in any way.

EXAMPLE 1

Preparation of N-hydroxy-N-[3-[2-(4-fluorophenylthio)-6-fluorophenyl]-prop-2-enyl]urea A.
2-[2-(4-fluorophenylthio)-6-fluorophenyl]-4,4-dimethyloxazoline To a solution of 4-fluorothiophenol (3.64 g, 28.4 mmol) in 50 ml of dry THF at −78° C. is added n-butyllithium (17.8 ml of a 1.6M solution in hexane). After 30 minutes, 2-(2,6-difluorophenyl)-4,4-dimethyloxazoline (5.0 g, 23.7 mmol) in 10 ml of dry THF is added dropwise. The reaction mixture is allowed to warm to room temperature and then is heated to 60° C. for 5.5 hours. After cooling, the reaction mixture is poured into water and then extracted with diethyl ether. The extracts are washed with water and then brine, and dried over MgSO₄ to afford the crude product. Chromatography over silica gel eluting with 10:1 hexane/ethyl acetate afforded the subtitle compound.

| Elemental Analysis: | C | H | N | S | F |
|---|---|---|---|---|---|
| Calculated | 63.93 | 4.73 | 4.39 | 10.04 | 11.90 |
| Found | 63.69 | 4.75 | 4.39 | 10.41 | 11.61 | m.p. 118-20° C.

B. 2-(4-fluorophenylthio)-6-fluorobenzoic acid

The compound 2-[2-(4-fluorophenylthio)-6-fluorophenyl]-4,4-dimethyloxazoline (5.0 g, 15.66 mmol) is added to 310 ml of a 4.5N HCl solution in water and is refluxed overnight. The cooled reaction mixture is extracted twice with ethyl acetate. The extracts are washed with water and then brine and dried over MgSO₄ to afford the subtitle compound.

C. 2-(4-fluorophenylthio)-6-fluorobenzyl alcohol

LiAlH₄ (0.77 g, 20.4 mmol) is suspended in 30 ml of dry diethyl ether with cooling in an ice bath. 2-(4--fluorophenylthio)-6-fluorobenzoic acid (4.53 g, 17.0 mmol) in 6 ml of diethyl ether and 6 ml of THF is then added and the reaction mixture stirred at room temperature overnight. The reaction mixture is quenched sequentially with 0.8 ml of water, 0.8 ml of 15% NaOH aqueous solution, and 2.4 ml of water. The resulting white precipitate is filtered off and washed thoroughly with diethyl ether. The filtrate and washings are combined and concentrated to afford the subtitle compound.

D. 2-(4-fluorophenylthio)-6-fluorobenzaldehyde

Pyridinium dichromate (8.34 g, 22.2 mmol) is suspended in 30 ml of methylene chloride. A solution of 2-(4-fluorophenylthio)-6-fluorobenzyl alcohol (3.73 g, 14.8 mmol) in 10 ml of methylene chloride is then added dropwise to the suspension. The reaction mixture is then stirred overnight. The reaction mixture is filtered through diatomaceous earth (Celite®) and then through silica gel to afford the subtitle compound. m.p. 94°-97° C.

E. 1-[2-(4-fluorophenylthio)-6-fluorophenyl]prop-2-en-1-ol 2-(4-fluorophenylthio)-6-fluorobenzaldehyde (2.06 g, 8.23 mmol) is dissolved in 21 ml of dry THF and cooled to −78° C. Vinylmagnesium bromide solution (12.4 ml of a 1.0M solution in THF) is then added dropwise and the reaction mixture is allowed to warm to room temperature. The reaction mixture is then poured into saturated NH₄Cl and extracted twice with diethyl ether. The extracts are washed with water and then brine and dried over K₂CO₃ to afford the subtitle compound.

F. 1-[2-(4-fluorophenylthio)-6-fluorophenyl]3-bromoprop-1-ene.

1-(2-(4-fluorophenylthio)-6-fluorophenyl)prop-2-en-1-ol (2.29 g, 8.23 mmol) is dissolved in 10 ml of hexane and 10 ml of diethyl ether and cooled in an ice bath. Concentrated HBr acid (4.6 ml, 41.2 mmol) is then added dropwise and the reaction mixture is stirred vigorously for 5 hours at room temperature. The reaction mixture is then poured into water and extracted twice with diethyl ether. The extracts are washed with water and then brine and dried over MgSO₄ to afford the subtitle compound.

G. N-[3-[2-(4-fluorophenylthio)-6-fluorophenyl]prop-2-enyl]-O-tetrahydropyranyl hydroxylamine O-tetrahydropyranylhydroxylamine (2.88 g, 24.6 mmol) is dissolved in 15 ml of dry DMF. A solution of 1-[2-(4-fluorophenylthio)-6-fluorophenyl]3-bromoprop-1-ene (2.80 g, 8.2 mmol) in 6 ml of DMF is added and the reaction is stirred for 4 hours at room temperature. The reaction mixture is poured into 200 ml of water and then extracted twice with diethyl ether. The extracts are washed three times with water and then with brine and dried over MgSO₄ to afford the crude product. Chromatography on silica gel eluting with 5:1 hexane/ethyl acetate afforded the subtitle compound.

H. N-[3-[2-(4-fluorophenylthio)-6-fluorophenyl]prop-2-enyl]hydroxylamine

N-[3-[2-(4-fluorophenylthio)-6-fluorophenyl]prop-2-enyl]-O-tetrahydropyranyl hydroxylamine (1.26 g, 3.34 mmol) is dissolved in 17 ml of methanol and cooled in an ice bath. Concentrated HCl (1.7 ml) is then added dropwise and the reaction mixture is stirred overnight at room temperature. The reaction mixture is evaporated to dryness and then slurried in saturated NaHCO₃ solution and extracted twice with diethyl ether. The extracts are washed with water and then brine and dried over K₂CO₃ to afford the subtitle compound.

I. N-hydroxy-N-[3-[2-(4-fluorophenylthio)-6-fluorophenyl]prop-2-enyl]urea

N-[3-[2-(4-fluorophenylthio)-6-fluorophenyl]prop-2-enyl]hydroxylamine (0.91 g, 3.1 mmol) is dissolved in 16 ml of dry dioxane. Trimethylsilyl isocyanate (0.36 g, 3.1 mmol) is then added dropwise and the reaction mixture is stirred at room temperature overnight. The reaction mixture is poured into 1N HCl solution and then extracted twice with diethyl ether. The extracts are washed with water and then with brine and dried over K₂CO₃ to afford the crude product. Recrystallization from ethyl acetate afforded the subtitle compound.

| Elemental Analysis: | C | H | N | S | F |
|---|---|---|---|---|---|
| Calculated | 57.13 | 4.19 | 8.33 | 9.53 | 11.29 |
| Found | 57.42 | 4.32 | 8.18 | 9.27 | 11.11 | mp. 138-139.5

EXAMPLE 2

Preparation of N-hydroxy-N-[3-[2-(4-fluorphenylthio)phenyl]prop-2-enyl]urea

A. 1-(2-bromophenyl)prop-2-en-1-ol

To 2-bromobenzaldehyde (27 g; 0.146 mmol.) in dry tetrahydrofuran cooled to −78° C. in a dry ice/isopropyl alcohol bath was added 175 ml of a 1.0M solution of vinyl Grignard reagent in tetrahydrofuran dropwise and the reaction allowed to slowly warm overnight to room temperature. The reaction mixture was quenched with saturated NH₄Cl and the tetrahydrofuran was concentrated off. The reaction mixture was poured into water and extracted twice with diethylether, washed with water and then brine and dried over $K_2CO_3$ to afford the subtitle compound.

B.
1-tetrahydropyranyloxy-1-(2-bromophenyl)-prop-2-ene

To 1-(2-bromophenyl)prop-2-en-1-ol) (31.0 g; 0.145 mol) in 150 ml of dry THF (tetrahydrofuran) was added 20 ml of 3,4-dihydro-2H-pyran and then 1 ml of $POCl_3$ and the mixture stirred over the weekend at room temperature. The reaction mixture was neutralized with saturated $NaHCO_3$ and concentrated down. The resulting material was partitioned between water and diethyl ether and the aqueous layer extracted again with diethyl ether. The organics were combined and washed with water and then brine and dried over $K_2CO_3$ and concentrated. The crude subtitle compound was chromatographed by HPLC using a solvent gradient from pure hexane to 5% ethyl acetate in hexane to afford the subtitle compound.

C.
1-tetrahydropyranyloxy-1-[2-(4-fluorophenylthio)-phenyl]prop-2-ene

To 1-tetrahydropyranyloxy-1-(2-bromophenyl)prop-2-ene (5.39 g; 18.1 mmol) in 60 ml of dry THF cooled to −78° C. was added n-butylithium (12.5 ml of 1.6M solution in hexane) and the reaction mixture stirred for five minutes. To the reaction mixture was added 4-fluorophenyldisulfide (5.54 g; 18 mmol) in 15 ml of dry THF. The cooling bath was removed and the reaction mixture allowed to warm to room temperature. The mixture was quenched with saturated $NH_4Cl$, and extracted twice with diethyl ether. The organics were washed twice with water and then with brine, dried over $MgSO_4$, and concentrated. HPLC of the crude subtitle compound using hexane and then 20:1 hexane/diethyl ether afforded the subtitle compound.

D.
1-[(2-(4-fluorophenylthio)phenyl]-3-bromoprop-1-ene

To 1-tetrahydropyranyloxy-1-[2-(4-fluorophenylthio)phenyl]prop-2-ene (2.71 g; 7.87 mmol) in 20 ml of diethyl ether under nitrogen cooled in an ice bath, was added concentrated HBr and the mixture stirred at 0° C. for one hour. The ice bath was removed and the reaction mixture stirred at room temperature overnight. The reaction mixture was poured into water and extracted twice with hexane. The organics were collected and washed with water and then brine and dried over $MgSO_4$ and concentrated to afford the subtitle compound.

E.
N-[3-[2-(4-fluorophenylthio)phenyl]prop-2-enyl]-O-tetrahydropyranyl hydroxylamine To O-tetrahydropyranyl hydroxylamine (2.77 g; 23.6 mmol) in 10 ml of dry dimethylformamide was added 1-[2-(4-fluorophenylthio)phenyl]-3-bromoprop-1-ene (2.54 g; 7.87 mmol) in 10 ml of dimethylformamide dropwise. The reaction mixture was stirred overnight at room temperature. The mixture was poured into 200 ml of water and extracted twice with diethyl ether. The organics were collected, washed twice with water and then with brine, dried over $K_2CO_3$ and concentrated. The crude subtitle compound was chromatographed by HPLC using 3:1 hexane/ethyl acetate and then 2:1 hexane/ethyl acetate to afford the subtitle compound.

F.
N-[3-[2-(4-fluorophenylthio)phenyl]prop-2-enyl]hydroxylamine

To N-[3-[2-(4-fluorophenylthio)phenyl]prop-2-enyl]-O-tetrahydropyranyl hydroxylamine (1.76 g; 4.9 mmol) in 25 ml of methanol and cooled in an ice bath was added 2.5 ml of concentrated HCl dropwise. The reaction mixture was stirred at room temperature overnight and then concentrated to dryness. The mixture was partitioned between diethyl ether and saturated $NaHCO_3$ and the aqueous layer extracted one more time with diethyl ether. The organics were combined, washed with water and brine and dried over $K_2CO_3$ to afford the subtitle compound.

G.
N-hydroxy-N-[3-(2-fluorophenylthio)phenyl]prop-2-enyl]urea

To N-[3-[2-(4-fluorophenylthio)phenyl]prop-2-enyl]-hydroxylamine (1.30 g; 4.7 mmol) in 24 ml of dry dioxane was added trimethylsilylisocyanate dropwise and the reaction mixture stirred at room temperature overnight. The mixture was poured into saturated $NH_4Cl$ and extracted twice with diethyl ether. The organics were combined, washed with 1N HCl and twice with water, and then brine, and dried over $MgSO_4$. The solids were recrystallized from ethyl acetate and washed with cold diethyl ether to afford 0.76 g of the subtitle compound mp 124°–125° C.

| Elemental Analysis: | C | H | N | S |
|---|---|---|---|---|
| Calculated | 60.36 | 4.75 | 8.80 | 10.07 |
| Found | 60.54 | 4.75 | 8.66 | 9.85 |

EXAMPLE 3

Preparation of N-hydroxy-N-[3-[2-(4-fluorophenylthio)-4-fluorophenyl]prop-2-enyl]urea A. To 2-[2-(4-fluorophenylthio)-4-fluorophenyl]-4,4-dimethyloxazoline.

To 4-fluorothiophenol (9.26 g; 72.2 mmol.) in dry THF under nitrogen and cooled to −78° C. was added n-butyllithium (45.2 ml of 1.6M) dropwise affording a white slurry. To this mixture was added 2-(2,4-difluorophenyl)-4,4-dimethyloxazoline (7.63 g; 36.1 mmol.) in 20 ml of dry THF dropwise. The reaction mixture was allowed to warm to room temperature overnight. An additional 50 ml of THF was added to afford a solution and the reaction stirred over the weekend. The mixture was poured into water, acidified to pH 5 with 1N HCl. The mixture was extracted twice with diethyl ether and the organics combined, washed with water and then 0.2N NaOH. The organic layer was washed again with water and then brine, dried over $MgSO_4$, and concentrated to afford 13.2 g of crude product which after recrystallization from hexane afforded 8.82 g of the subtitle compound.

B.
N-hydroxy-N-[3-[2-(4-fluorophenylthio)-4-fluorophenyl]prop-2-enyl]urea

By substantially following the procedures described above in Example 1, Steps B to the end, the subtitle compound was afforded. After recrystallization from ethyl acetate 0.94 g of the desired subtitle compound was afforded; mp 151°–153° C.

| Elemental Analysis: | C | H | N | S | F |
|---|---|---|---|---|---|
| Calculated | 57.13 | 4.20 | 8.33 | 9.53 | 11.30 |
| Found | 57.11 | 4.39 | 8.52 | 9.36 | 11.60 |

EXAMPLE 4

Preparation of N-hydroxy-N-[3-[2-(4-fluorophenylthio)-5-fluorophenyl]prop-2-enyl]urea By substantially following the procedures described above in Example 3 and using the appropriately substituted, 2-(2,5-difluorophenyl)-4,4-dimethyl oxazoline, 0.31 g of the title compound was obtained after recrystallization from ethyl acetate.

| Elemental Analysis: | C | H | N | S | F |
|---|---|---|---|---|---|
| Calculated | 57.13 | 4.20 | 8.33 | 9.53 | 11.30 |
| Found | 57.32 | 4.16 | 8.10 | 9.57 | 11.50 |

EXAMPLE 5

Preparation of N-hydroxy-N-[3-[2-(4-chlorophenylthio)phenyl]prop-2-enyl]urea

By substantially following the procedures as described above in Example 1, Steps E to the end, the title compound was prepared from the commercially available compound 2-[(4-chlorophenyl)thio]benzaldehyde. mp. 126°–128° C.

| Elemental Analysis: | C | H | N |
|---|---|---|---|
| Calculated | 57.40 | 4.52 | 8.37 |
| Found | 57.54 | 4.41 | 8.37 |

EXAMPLE 6

Preparation of N-hydroxy-N-[3-[2-(4-fluorophenylthio)-3-fluorophenyl]prop-2-enyl]urea By substantially following the procedures described above in Example 1, the title compound was prepared. mp. 127°–128° C.

| Elemental Analysis: | C | H | N | S | F |
|---|---|---|---|---|---|
| Calculated | 57.13 | 4.19 | 8.33 | 9.53 | 11.39 |
| Found | 57.12 | 4.15 | 8.27 | 9.69 | 11.85 |

EXAMPLE 7

Preparation of N-hydroxy-N-[3-[2-(4-chlorophenylthio)-3-fluorophenyl]prop-2-enyl]urea By substantially following the procedures described above in Example 3, the title compound was prepared. mp 125°–127° C.

| Elemental Analysis: | C | H | N | S | Cl | F |
|---|---|---|---|---|---|---|
| Calculated | 54.47 | 4.00 | 7.94 | 9.09 | 10.05 | 5.38 |
| Found | 54.39 | 4.00 | 7.65 | 8.83 | 10.00 | 5.69 |

EXAMPLE 8

Preparation of N-hydroxy-N-[3-[2-4-chlorophenylthio)-6-fluorophenyl]prop-2-enyl]urea.

By substantially following the procedures described above in Example 3, the title compound was prepared. mp. 137°–139° C.

| Elemental Analysis: | C | H | N | S | Cl | F |
|---|---|---|---|---|---|---|
| Calculated | 54.47 | 4.00 | 7.94 | 9.09 | 10.05 | 5.38 |
| Found | 54.67 | 4.00 | 7.78 | 9.24 | 10.03 | 5.66 |

As noted above, the compounds of the present invention are useful for inhibiting the conversion of arachidonic acid by 5-lipoxygenase to 5-hydroperoxy-6,8,11,14-eicosatetraenoic acid (5-HPETE). Therefore, another embodiment of the present invention is a method for inhibiting the conversion of arachidonic acid into leukotrienes which comprises adminiserting to a mammal in need of 5-lipoxygenase inhibition an effective amount of a compound according to Formula I or a pharmaceutically acceptable salt thereof.

The term "effective amount" as used herein, means an amount of a compound of the present invention which is capable of inhibiting the first step of the biochemical synthesis pathway by which arachidonic acid is converted into leukotrienes which is catalyzed by the enzyme 5-lipoxygenase and particularly, inhibiting 5-lipoxygenase. The 5-lipoxygenase inhibition contemplated by the present method includes both medical therapeutic and/or prophylactic treatment, as appropriate. The specific dose of compound administered according to this invention will, of course, be determined by the particular circumstances surrounding the case, including, for example, the compound administered, the route of administration, and the condition being treated. A typical daily dose will contain form about 0.01 mg/kg to about 20 mg/kg of the active compound of this invention. Preferred daily doses generally will be from about 0.05 to about 10 mg/kg and ideally from about 0.1 to about 5 mg/kg.

The compounds can be administered by a variety of routes including oral, rectal, transdermal, subcutaneous, intravenous, intramuscular, and intranasal. A special feature of the compound of this invention is that they have high potency and therefore lowered dosages are capable of effectively inhibiting the 5-LO catalyzed reaction.

A variety of physiologic functions have been associated with leukotrienes. As such, the compounds of this invention are believed to have the ability to treat in mammals a variety of disorders associated with leukotrienes such as asthma and allergic diseases, (including allergic rhinitis) inflammatory bowel disease, psoriasis, shock, ischemia, adult respiratory distress syndrome and arthritis. Therefore, the present invention also provides methods of treating the above disorders at the rates set forth above for inhibiting the 5-lipoxygenase catalyzed conversion of arachidonic acid to leukotrienes, by administering to a mammal in need of 5-lipoxygenase inhibition an asthma, allergic disease, inflammatory bowel disease, psoriasis, shock, ischemia, adult respiratory distress syndrome or arthritis relieving dose of a compound of the present invention.

The compounds of the present invention are preferably formulated prior to administration. Therefore, another embodiment of the present invention is a pharmaceutical formulation comprising an effective amount of a compound of Formula I or a pharmaceutically acceptable salt thereof and a pharmaceutically acceptable carrier, diluent or excipient therefor.

The active ingredient in such formulations comprises from 0.1% to 99.9% by weight of the formulation. By pharmaceutically acceptable it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gumacacia, calcium phosphate, alginates, tragacanth, gelatin, calcium silicate, microcrystalline cellulose, polyvinylpyrrolidone, cellulose, water syrup, methyl cellulose, methyl-hydroxybenzoates, propylhydroxybenzoates, talc, magnesium stearate and mineral oil. The formulations may additionally include lubricating agents, wetting agents, sweetening agents, flavoring agents, and the like. The compositions of the invention may be formulated so as to provide quick, sustained or delayed release of the active ingredient after administration to the patient by employing procedures well known in the art.

The compositions are preferably formulated in a unit dosage form, each dosage generally containing from about 0.1 to about 500 mg, and preferably from about 1 to about 250 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way. "Active ingredient", of course, means a compound according to Formula I or a pharmaceutically acceptable salt thereof.

FORMULATION 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

The above ingredients are mixed and filled into hard gelatin capsules in 460 mg quantities.

FORMULATION 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

FORMULATION 3

An aerosol solution is prepared containing the following components:

|  | Weight % |
|---|---|
| Active ingredient | 0.25 |
| Ethanol | 29.75 |
| Propellant 22 (chlorofdifluoromethane) | 70.00 |
| Total | 100.00 |

The active compound is mixed with ethanol and the mixture added to a portion of the propellant 22, cooled to $-30°$ C. and transferred to a filling device. The required amount is then fed to a stainless steel container and diluted with the remainder of the propellant. The valve units are then fitted to the container.

FORMULATION 4

Tablets, each containing 60 mg of active ingredient, are made as follows:

| Active ingredient | 60 mg |
|---|---|
| Starch | 45 mg |
| Microcyrstalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

| Active ingredient | 225 mg |
|---|---|
| Saturated fatty acid glycerides | 2,000 mg |
| Total | 2,225 mg. |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, such containing 50 mg of active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| Active ingredient | 100 mg |
|---|---|
| Sodium alginate | 500 mg |
| Isotonic saline | 1,000 ml |

The solution of the above ingredients generally is administered intravenously to a subject at a rate of 1 ml per minute.

The following experiments were carried out to demonstrate the ability of the compounds of the present invention to inhibit 5-lipoxygenase.

Sensitization procedures

Male, Hartley strain guinea-pigs (200–250 g) were actively sensitized by three injections of ovalbumin (OA, 10 mg/kg). The OA was administered intraperitoneally on Days 1 and 3 and subcutaneously on Day 5. In vitro experiments were performed 21–25 days later.

General In vitro

On the day of the experiment, guinea pigs were killed by asphyxiation with $CO_2$ and the tracheas removed, cleaned of surrounding connective tissue and cut into spiral strips. Each strip was divided in half for paired experiments. Tissues were placed in 10 ml jacketed tissue baths maintained at 37° C. and attached with cotton thread to Grass force-displacement transducers (FT03C). Changes in isometric tension were displayed on a Grass polygraph (Model 7D). Tracheal strips were bathed in modified Krebs' solution of the following composition (millimolar) NaCl, 118.2; KCl, 4.6; $CaCl_2.2H_2O$, 2.5; $MgSO_4.7H_2O$, 1.2; $NaHCO_3$, 24.8; $KH_2PO_4$, 1.0; and dextrose, 10.0. The buffer contained indomethacin (5 $\mu M$) which potentiated the contractions of the cysteinyl leukotriene (LT) by removing the influence of cyclooxygenase products. The tissue baths were aerated with 95% $O_2$:5% $CO_2$. Tracheal strips were placed under a resting tension of 2 g, and the tissues were allowed a minimal stabilization period of 60 minutes before undergoing experimentation. Bath fluid was changed at 15 minute intervals during the stabilization period.

Concentration-response curves

Cumulative concentration-response curves were obtained from tracheal strips by increasing the agonist concentration in the organ bath by half-log increments while the previous concentration remained in contact with the tissues (van Rossum, *Arch. Int. Pharmacodyn. Ther.*, 143, 299–330 (1963)). Agonist concentration was increased after reaching the plateau of the contraction elicited by the preceeding concentration. One concentration-response curve was obtained from each tissue. To minimize variability between tissues, contractile responses were expressed as a percentage of the maximal response obtained with carbachol (10 $\mu M$), added to the bath at the end of the concentration-response curve. Initially, tissues were challenged with carbachol (10 $\mu M$) following the 60 minute stabilization period to insure tissue viability. After recording the maximal response to the initial carbachol challenge, the tissues were washed and reequilibrated for 60 minutes before starting the experimental protocol.

Determination of $EC_{50}$ and % Inhibition

To evaluate the effects of novel 5-lipoxygenase inhibitors in the Schultz-Dale reaction, each compound was incubated with the tissues 30 minutes before starting the curves. Vehicle (DMSO) was given to the paired control tissue. Pyrilamine (10 $\mu M$) was added to all baths at this time to block the actions of released histamine. Responses obtained at the antigen concentration of 30 ng/ml were recorded in the absence and presence of drug and percent inhibition was calculated for each pair of tissues. $IC_{50}$ valves were determined by linear regression.

LT or carbachol concentration-response curves were used to determine specificity of the agent as a 5-lipoxygenase inhibitor. In these experiments the test compound was incubated as described above. $EC_{50}$ values, which represent the molar concentration of agonist required to induce 50% of maximal response, was determined by linear regression. Differences in $EC_{50}$ values, in the presence and absence of test compound were analyzed by Student's t-test with $P<0.05$ regarded as significant.

In vivo studies

Male Hartley guinea pigs (350–500 g) were passively sensitized against ovalbumin by i.p. administration of 0.3 ml of antiserum 2 days preceeding the experiment. Hyperimmune serum was prepared from actively sensitizing male guinea pigs conditioned with 2 mg of ovalbumin in 50% Complete Freund's Adjuvant i.p. on days 1 and 5. On day 21, the animals were bled and the serum collected and stored at $-20°$ C. On the day of the experiment the passively sensitized guinea pigs were anesthetized with 35 to 40 mg/kg of pentobarbital sodium given i.p. The right jugular vein was cannulated with Tygon microbore tubing (o.d.=03) connected to a syringe for administration of selected drugs. Blood pressure was measured with a Statham pressure transducer connected to a Tygon catheter placed in the left carotid artery. The trachea was cannulated and each animal was ventilated with room air by means of a Harvard rodent respirator set to deliver a tidal volume of 1 ml/100 g body weight with a rate of 60 breaths/minute. Succinylcholine (5 mg/kg) was given i.v. to suppress spontaneous respiration. Intratracheal pressure, an index of total pulmonary resistance, was measured with a Statham pressure transducer connected to a T-tube on the tracheal cannula. Output signals from the pressure transducers were displayed on a Grass polygraph. Body temperature was maintained within normal limits by means of a Deltaphase isothermal pad. Prior to surgery, test compound or vehicle (PEG 400) was administered to each guinea pig by oral gavage and OA challenge was at designated times following oral dosing. The animals were pretreated i.v. with pyrilamine (5 mg/kg), propranolol (1 mg/kg) and indomethacin (10 mg/kg) 5 minutes prior to the OA challenge. OA-induced increase in tracheal pressure was expressed as a percentage of the maximal pressure obtained by clamping the trachea with a hemistat. To determine the effect of each drug, a % inhibition value was calculated from the vehicle and drug treated animals at each concentration tested.

TABLE I

| | Inhibition of 5-LO | |
|---|---|---|
| Example No. | In Vitro $IC_{50}$ μM | In Vivo Percent Inhibition at 30 mg/kg, po, 2 hr. |
| 1 | 0.05 | 97 |
| 2 | 0.10 | 96 |
| 3 | 0.19 | 43[a] |
| 4 | 0.23 | 52 |
| 5 | 0.14 | 95 |
| 6 | 0.13 | 81 |
| 7 | 0.09 | 77[a] |
| 8 | 0.13 | 46 |

Note:
[a]dose of 10 mg/kg

It should be understood that the instant specification and examples are set forth by way of illustration and not limitation, and that various modifications and changes may be made without departing from the spirit and scope of the present invention as defined by the appended claims.

We claim:

1. An N-hydroxy-N-[3-[2-(halophenylthio)phenyl]-prop-2-enyl]urea of the Formula

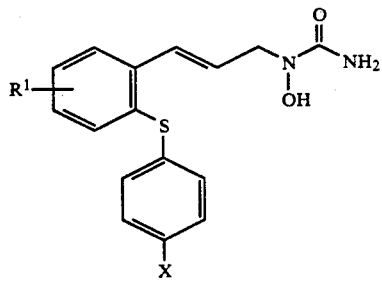

where
$R^1$ is hydrogen or halo;
X is fluoro or chloro; and pharmaceutically acceptable salts thereof.

2. A compound according to claim 1 wherein:
$R^1$ is halo; and pharmaceutically acceptable salts thereof.

3. A compound according to claim 2 wherein $R^1$ is fluoro.

4. A compound according to claim 3 which is selected from:

N-hydroxy-N-[3-[2-(4-fluorophenylthio)-5-fluorophenyl]prop-2-enyl]urea;

N-hydroxy-N-[3-[2-(4-fluorophenylthio)-4-fluorophenyl]prop-2-enyl]urea;

N-hydroxy-N-[3-[2-(4-fluorophenylthio)-3-fluorophenyl]prop-2-enyl]urea;

N-hydroxy-N-[3-[2-(4-chlorophenylthio)-6-fluorophenyl]prop-2-enyl]urea;

N-hydroxy-N-[3-[2-(4-chlorophenylthio)-3-fluorophenyl]prop-2-enyl]urea; and pharmaceutically acceptable salts thereof.

5. A compound according to claim 1 wherein:
R1 is hydrogen; and pharmaceutically acceptable salts thereof.

6. A compound according to claim 5 which is N-hydroxy-N-[3-[2-(4-chlorophenylthio)phenyl]prop-2-enyl]urea and pharmaceutically acceptable salts thereof.

7. A compound according to claim 5 which is N-hydroxy-N-[3-[2-(4-fluorophenylthio)phenyl]prop-2-enyl]urea; and pharmaceutically acceptable salts thereof.

8. A pharmaceutical composition comprising a pharmaceutically acceptable carrier, diluent or excipient and a compound having the Formula

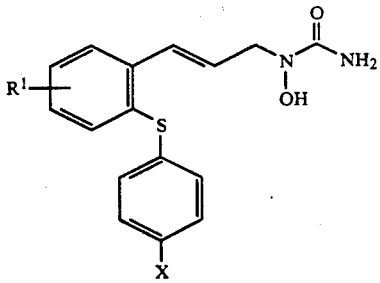

where
R1 is hydrogen, or halo;
X is fluoro or chloro; or a pharmaceutically acceptable salt thereof.

9. A pharmaceutical composition according to claim 8 wherein:
R1 is halo; and pharmaceutically acceptable salts thereof.

10. A pharmaceutical composition according to claim 9 wherein:
R1 is fluoro; and pharmaceutically acceptable salts thereof.

11. A pharmaceutical composition according to claim 10 wherein said compound is selected from:
N-hydroxy-N-[3-[2-(4-fluorophenylthio)-5-fluorophenyl]prop-2-enyl]urea;
N-hydroxy-N-[3-[2-(4-fluorophenylthio)-4-fluorophenyl]prop-2-enyl]urea;
N-hydroxy-N-[3-[2-(4-fluorophenylthio)-3-fluorophenyl[-prop-2-enyl]urea;
N-hydroxy-N-[3-[2-(4-chlorophenylthio)-6-fluorophenyl]prop-2-enyl]urea;
N-hydroxy-N-[3-[2-(4-chlorophenylthio)-3-fluorophenyl]prop-2-enyl]urea; and pharmaceutically acceptable salts thereof.

12. A pharmaceutical composition according to claim 8 wherein R¹ is hydrogen; and pharmaceutically acceptable salts thereof.

13. A pharmaceutical composition according to claim 12 wherein said compound is N-hydroxy-N-[3-[2-(4-chlorophenylthio)phenyl]prop-2-enyl]urea; pharmaceutically acceptable salts thereof.

14. A pharmaceutical composition according to claim 12 wherein said compound is N-hydroxy-N-[3-[2-(4-fluorophenylthio)phenyl]prop-2-enyl]urea; and pharmaceutically acceptable salts thereof.

15. A method of inhibiting 5-lipoxygenase comprising administering to a mammal in need of 5-lipoxygenase inhibition a 5-lipoxygenase inhibiting dose of a compound of the Formula

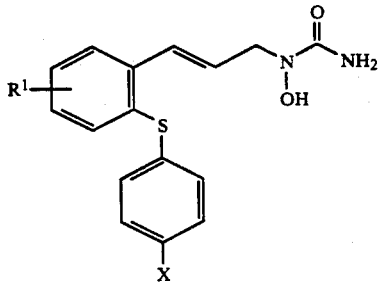

where:
R1 is hydrogen; or halo;
X is fluoro or chloro; and pharmaceutically acceptable salts thereof.

16. A method of treating asthma, arthritis, allergy, inflammatory bowel disease, psoriasis, shock, adult respiratory distress syndrome or ischemia in a mammal suffering from said condition by administering a condition relieving dose of a compound having the Formula:

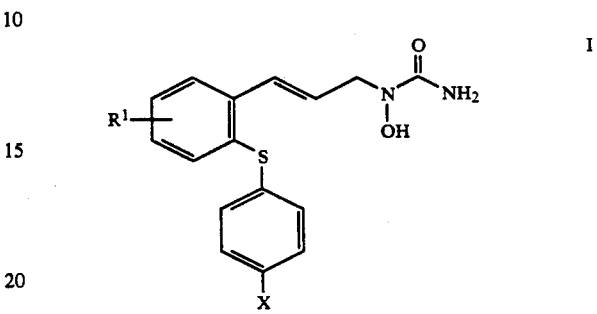

where:
R¹ is hydrogen or halo
X is fluoro or chloro; and pharmaceutically acceptable salts thereof.

17. A method according to claim 16 wherein:
R¹ is halo; and pharmaceutically acceptable salts thereof.

18. A method according to claim 17 wherein:
R¹ is fluoro; and pharmaceutically acceptable salts thereof.

19. A method according to claim 18 wherein said compound is selected from:
N-hydroxy-N-[3-[2-(4-fluorophenylthio)-5-fluorophenyl]prop-2-enyl]urea;
N-hydroxy-N-[3-[2-(4-fluorophenylthio)-4-fluorophenyl]prop-2-enyl]urea;
N-hydroxy-N-[3-[2-(4-fluorophenylthio)-3-fluorophenyl]-prop-2-enyl]urea;
N-hydroxy-N-[3-[2-(4-chlorophenylthio)-6-fluorophenyl]prop-2-enyl]urea;
N-hydroxy-N-[3-[2-(4-chlorophenylthio)-3-fluorophenyl]prop-2-enyl]urea; and pharmaceutically acceptable salts thereof.

20. A method according to claim 16 wherein R¹ is hydrogen; and pharmaceutically acceptable salts thereof.

21. A method according to claim 20 wherein said compound is N-hydroxy-N-[3-[2-(4-chlorophenylthio)-phenyl]prop-2-enyl]urea; and pharmaceutically acceptable salts thereof.

22. A method according to claim 20 wherein said compound is N-hydroxy-N-[3-[2-(4-fluorophenylthio)-phenyl]prop-2-enyl]urea; and pharmaceutically acceptable salts thereof.

23. A compound according to claim 3 which is N-hydroxy-N-[3-[2-(4-fluorophenylthio)-6-fluorophenyl]-prop-2-enyl]urea and pharmaceutically acceptable salts thereof.

24. A pharmaceutical composition according to claim 10 wherein said compound is N-hydroxy-N-[3-[2-(4-fluorophenylthio)-6-fluorophenyl]prop-2-enyl]urea and pharmaceutically acceptable salts thereof.

25. A method according to claim 18 wherein said compound is N-hydroxy-N-[3-[2-(4-fluorophenylthio)-6-fluorophenyl]prop-2-enyl]urea and pharmaceutically acceptable salts thereof.

* * * * *

UNITED STATES PATENT AND TRADEMARK OFFICE
CERTIFICATE OF CORRECTION

PATENT NO. : 5,283,361

DATED : Feb. 1, 1994

INVENTOR(S) : Gary A. Hite, et al.

It is certified that an error appears in the above-identified patent and that said Letters Patent is hereby corrected as shown below:

Column 1, line 53 "...substituted..." should read --...substituent...--

Column 14, lines 10 and 11 "N-hydroxy-N-[3-[2-4-chlorophenylthio)-6-fluorophenyl]prop-2-enyl]urea." should read --N-hydroxy-N-[3-[2-(4-chlorophenylthio)-6-fluorophenyl]prop-2-enyl]urea.--.

Column 21, lines 45 and 46 "...urea; pharmaceutically acceptable salts thereof." should read --...urea; and pharmaceutically acceptable salts thereof.--

Signed and Sealed this

Eleventh Day of October, 1994

Attest:

BRUCE LEHMAN

Attesting Officer

Commissioner of Patents and Trademarks